(12) United States Patent
Eliaz (10) Patent No.: US 11,058,714 B2
(45) Date of Patent: Jul. 13, 2021

(54) ADMINISTRATION OF SYNERGISTIC AMOUNTS OF MODIFIED CITRUS PECTIN AND HONOKIOL TO TREAT INFLAMMATION AND ANTI-OXIDANT NEEDS

(71) Applicant: ECONUGENICS INC, Santa Rosa, CA (US)

(72) Inventor: Isaac Eliaz, Santa Rosa, CA (US)

(73) Assignee: ECONUGENICS, INC., Santa Rosa, CA (US)

( * ) Notice: Subject to any disclaimer, the term of this patent is extended or adjusted under 35 U.S.C. 154(b) by 0 days.

(21) Appl. No.: 16/439,563

(22) Filed: Jun. 12, 2019

(65) Prior Publication Data
US 2019/0290679 A1 Sep. 26, 2019

Related U.S. Application Data

(63) Continuation-in-part of application No. 15/181,726, filed on Jun. 14, 2016, now abandoned.

(51) Int. Cl.
| | | |
|---|---|---|
| *A61K 31/732* | (2006.01) | |
| *A61K 31/05* | (2006.01) | |
| *A61K 9/00* | (2006.01) | |
| *A61K 9/46* | (2006.01) | |
| *A61P 29/00* | (2006.01) | |

(52) U.S. Cl.
CPC .......... *A61K 31/732* (2013.01); *A61K 9/0007* (2013.01); *A61K 9/0056* (2013.01); *A61K 31/05* (2013.01); *A61P 29/00* (2018.01)

(58) Field of Classification Search
None
See application file for complete search history.

(56) References Cited

U.S. PATENT DOCUMENTS

| | | | | |
|---|---|---|---|---|
| 4,097,604 A | * | 6/1978 | Thiele | A61K 8/361 |
| | | | | 424/49 |
| 2012/0244087 A1 | * | 9/2012 | Trivedi | A61K 8/9789 |
| | | | | 424/48 |

OTHER PUBLICATIONS

Noh, M. K., Jung, M. Kim, S. H., Lee, S. R., Park, K. H., Kim, D. H., . . . & Park, Y. G. (2013). Assessment of IL-6, IL-8 and TNF-α levels in the gingival tissue of patients with periodontitis. Experimental and therapeutic medicine, 6(3), 847-851. (Year: 2013).*

* cited by examiner

*Primary Examiner* — Dale R Miller
(74) *Attorney, Agent, or Firm* — The Kelber Law Group; Steven B. Kelber (57) ABSTRACT

A method of inhibiting or reducing inflammation in a mammal comprises administering MCP or similar Gal-3 binding moiety with honokiol in a range of about 8-10:1, by weight, MCP to honokiol. By pursuing complimentary pathways, a synergistic combination is achieved, where the reduction or degree of inflammation inhibition is greater than would be expected by the added administration of these two agents. The inflammation may be manifested as gingivitis, which may be addressed by a preparation comprising honokiol and MCP, or an MCP equivalent, in the indicated range by weight, where they are in the form of an oral rinse, lozenge, sucking candy, toothpaste or tablet.

5 Claims, 6 Drawing Sheets

ADMINISTRATION OF SYNERGISTIC AMOUNTS OF MODIFIED CITRUS PECTIN AND HONOKIOL TO TREAT INFLAMMATION AND ANTI-OXIDANT NEEDS

CLAIM TO BENEFIT OF PRIORITY

This application is a continuation-in-part of U.S. patent application Ser. No. 15/181,726 filed Jun. 14, 2016. Applicant claims benefit of the filing date of the disclosure of U.S. patent application Ser. No. 15/181,726 pursuant to 35 U.S.C. § 120. The disclosure of U.S. patent application Ser. No. 15/181,726 is incorporated herein by reference in its entirety

BACKGROUND OF THE INVENTION

Field of the Invention

The present invention relates to the control of inflammation by the administration of well tolerated, safe ingredients and methods for doing the same. Although no claim to priority is made, this patent application is related to U.S. Pat. No. 8,416,567 by the same inventor directed to the administration of modified citrus pectin to improve immune response and U.S. Pat. No. 8,916,541 by the same inventor directed to the co-administration of honokiol and modified citrus pectin (MCP) to address certain forms of cancer. The disclosure of each prior patent is incorporated herein by reference.

Background of the Invention

Inflammation is a widespread phenomenon in animals, and occurs in almost every type of tissue. This invention is directed to the treatment of inflammation in mammals, particularly humans. Commercial mammals (cows, pigs, horses, etc.) and companion mammals (dogs, cats and the like) are particularly addressed, but the invention embraces within its scope of the treatment of model mammals such as apes and monkeys as well. All mammals are impacted by inflammation from time to time.

Inflammation can arise from a variety of sources and causes in general, inflammation embraces redness, swelling, an increase in local temperatures and the like, all in response to chemicals released by specialized cells, typically either leukocytes or lymphocytes. In many cases, inflammation is a response to invasion of the body by foreign bodies, typically either bacteria or viruses. In other situations, inflammation can arise from autoimmune diseases like rheumatoid arthritis and the like, where the body falsely believes there is an invader and responds to it. In other cases it can be a response to metabolic changes such as pH changes, changes in mitochondrial function, changes in circulation, hyperviscosity, reduced oxygenation and shift to glycolysis with increase in lactic acid, toxic exposure, ionizing and oxidizing agents, lack of antioxidant capacity, among others. Another example of inflammation is a response to changes occurring in the mammalian patient, like gingivitis. Gingivitis is a form of gum disease that happens when plaque, a naturally-occurring sticky film containing bacteria, builds up on teeth and causes inflammation of the surrounding gum tissue. The film may also comprise other agents, such as possible viruses, fungal agents and parasites. Plaque produces toxins that irritate the gums. This can cause the gums to become inflamed, making them red or puffy, or causing them to bleed. In general, inflammation is a response that may assist the body in concentrating and focusing its reserves in response to trauma, injury or infectious disease.

In many cases, however, the inflammation response exceeds the body's needs, or goes beyond the necessary response level. Inflammation can result in pain, discomfort and can interfere with both short and long term healing processes. In some tissues, such as nerve tissue, inflammation may be more difficult to control because access to the central nervous system by peripheral bodies in the blood and lymph may be blocked. Many different organ systems are adversely impacted by inflammation; inflammation of the cardiac, renal, pulmonary, and liver tissue among others may ultimately result in organ failure or a loss of organ function, even as the body tries to respond to challenge. In the case of more chronic degenerative diseases, ongoing inflammation becomes a driving force in progressive organ and systemic pathophysiology, altering tissue and organ architecture to promote fibrotic remodeling, resulting in progressive loss of function. Combined with other risk factors such as metabolic dysregulation, hypertension, etc., chronic inflammation has been shown to underlay the whole array of chronic diseases, including cardiovascular pathologies, chronic kidney, lung and liver disease, autoimmune and neurodegenerative diseases, and the process of aging itself.

Thus, it is frequently desirable to control or reduce the level of inflammation in a mammal suffering from the same. To this end, there are many products available, both manmade and natural. Corticosteroids are a mainstay of anti-inflammatory therapies for both acute situations and chronic inflammatory condition is where other agents have failed to be effective. Steroids are used commonly in such conditions as asthma and certain autoimmune conditions. However, they have a significant side effect profile when used on an ongoing basis. Aspirin is one of the most widely known anti-inflammatory agents, but it is only one of many. Other nonsteroidal anti-inflammatory drugs (NSAIDs) like ibuprofen and naproxen are also widely used. These also can have significant side effects when used long term, including gastric bleeding. There are also immune selective anti-inflammatory derivatives (ImSAIDs), peptides currently under development, said to have anti-inflammatory properties, but without some of the negative side-effects of NSAIDS. By the same token, there are a vast number of naturally occurring botanicals, like willow bark (which contains the chemical salicin, which is the precursor to aspirin), that either have been demonstrated to be effective anti-inflammatories or have had this character attributed to them.

Not enough is known about the actual mechanisms of action anti-inflammatories utilize to reduce inflammation. Obviously, not all inflammation should be reduced or eliminated. In many cases, inflammation serves to make us aware of a danger or injury, and is a means of the body focusing its resources. When inflammation exceeds that which is beneficial, even though there are many compounds and agents available to treat inflammation, not all work in all tissues. Many are dangerous to take, more dangerous to take in large amounts and even more dangerous to take over the long term. Like many medications, anti-inflammatories often do not work well together. Even though one agent might treat inflammation in one tissue, another might be better for the specific pain associated with inflammation in another tissue. When co-administered, they may not work well together or may magnify the side effect profile of either alone. The benefit obtained is not twice the benefit of giving one. Administration of an INSAID and an ImSAID has been shown to result in little improvement over administration of one or the other. Control of inflammation would be enhanced by co-administration of two drugs each of which works to reduce or control inflammation through a different body pathway, so as not to interfere with the actions of the other. In an ideal case, the action of one might potentiate the action of another. In such a situation, synergy of action can be observed, where the result of giving two different drugs is more than additive. In fact, a greater response is seen than administration of one agent added to the administration of another agent would be expected to provide. Ideally, co-administration of two agents would not increase side effects. Botanical extracts, many of which have been used for thousands of years in traditional medical systems, such as in Traditional Asian and Indian Medical systems, have minimal side effects and are co-administered with other botanicals that are known to mitigate potential side effects, provide supportive actions, and enhance the effectiveness of the primary herb in the formula. Thus there is a long traditional history of co-administration of botanicals for their synergistic action as perceived by clinical observation, prior to the advent of modern scientific analysis.

Honokiol is a very well known, well tolerated biologically active ingredient derived from magnolia bark, *Magnolia offinalis*. Honokiol has been shown in preclinical studies to be an effective anti-oxidant, used for a wide variety of conditions including dermatological disorders, Shen et al, *Molecules*, 15, 6452-6465 (2010) cancer prevention and therapy, Arora et al, *Curr. Mol. Med.*, 12(10), 1244-1252 (2012), neuro protection, Woodbury, et al, *Front Neurol.*, September 11; 4:130 (2013), cardiovascular conditions, Zhang, et al. *Biol Pharm Bull*. 33(3):427-31 (2010), metabolic disorders, Atanasov et al. *Biochim Biophys Acta*. October; 1830(10):4813-9 (2013) as an anxiolytic agent, Kuribara, et al, *J Pharm Pharmacol*., January; 51(1):97-103 (1999)., and others. The products of the *magnolia* tree, including honokiol, were explored in Lee et al, *Pharm. And Therapuetics*, 130(2):157-176 (2011). Among the many other pharmacological properties investigated were anti-inflammatory ones. A wide variety of inflammatory pathways were imputed to the action of honokiol. Among possible pathways, TNF-alpha expression may be suppressed by these agents. The potential activity of honokiol in decreasing TNF-alpha and IL-6 production was reported to offer promise in blocking autoimmune responses.

To further understand honokiol's anti-inflammatory effects, lipopolysaccharide (LPS) was used to induce inflammation; honokiol was found to decrease TNF-alpha secretion in mouse macrophages following LPS exposure. Additionally, honokiol inhibited nitric oxide expression in macrophages, protein kinase C-α membrane translocation, and NFκB activation, Chao et al, *J Agric Food Chem.*, 58(6):3472-810 (2010). This anti-inflammatory action can be translated to human monocyte-derived dendritic cells, Li et al, *J Cell Physiol.*, 226(9):2338-4910 (2011). These studies are supported by work from Murakami et al. *In Vivo*, 26(6):941-50 (2012) who found similar inhibitory effects of honokiol on NFκB activation and COX-2 expression. Honokiol may also act as a potent anti-inflammatory agent with multi-potential activities due to an inhibitory effect on the phosphoinositide 3-kinase (PI3K)/Akt pathway. Honokiol's anti-inflammatory effects seem to be mediated by interrupting the early activated intracellular signaling molecule PI3K/Akt, but not Src, the extracellular signal-regulated kinase, and p38, according to pharmacological, biochemical, and functional analyses, Kim et al. *Planta Med*. April; 71(4):338-43 (2005).

This inventor's own investigation of the ability of honokiol to suppress certain tumor formation led to the discovery of the synergistic combination of honokiol and modified citrus pectin (MCP) in the treatment of various forms of cancer, as reported and claimed in U.S. Pat. No. 8,916,541. As set forth therein, the honokiol, documented in the literature as effective in the treatment of certain cancers, can be combined with MCP in a range of about 9:1 MCP: honokiol (by weight) to give a synergistic effect in the treatment of cancer and inhibit the transformation of metastases.

MCP and its corresponding alginate derivatives, polysaccharides having a molecular weight of less than 40,000 Daltons, are well established as therapeutic agents. U.S. Pat. No. 7,026,302 as well as related U.S. Pat. Nos. 6,462,029 and 6,274,566 describe MCP products and alginates prepared by either hydrolysis or enzymatic digestion shown to be effective in treatment of a wide variety of poisoning and disease states. The disclosure of these patents is incorporated herein-by-reference. U.S. Pat. No. 7,451,871 also discloses the use of these modified citrus pectins and related compounds having a low enough molecular weight to be easily absorbed and systemically active, and having partially esterified galacturonic acid moieties as aids in controlling cancer metastases by binding the cancer emboli in the blood stream. Both the '871 patent, and U.S. patent application Ser. No. 11/485,955, which discloses that MCP can be used to enhance the immune system response of mammals, are incorporated herein-by-reference.

The antineoplastic effect of MCP is well documented. Gunning et al, *FASEB J.*, Vol. 23, 415-424 (2009) first reviews the demonstrated effectiveness of MCP against a variety of cancers, both in terms of inhibiting progression and metastases, and establishes that MCP binds, in vivo, the mammalian protein galectin-3 (Gal-3). Gal3 is a pro-inflammatory protein implicated in a number of different cancer cell progressions and metastatic conversions, and by binding this protein, the transformation of cells into cancerous cells may be inhibited, and the progression of existing cancers slowed. In addition to binding cancer emboli and suppressing metastases through these processes, MCP may also be effective in suppressing the conversion to metastatic forms. Yan and Katz, *Int. Cancer Ther.* 9 (2), 197-203 (2010). MCP has been shown to be effective in the treatment of, and inhibition of, prostate cancer, Pienta et al, *J. Natl. Cancer Inst.*, 24, 1854-62 (2002) as well as lung cancer, fibrosarcoma and melanoma. Kay et al, *Am. J. Clin. Nutr.*, 30, 171-175 (1997) as well as other solid tumors, such as breast cancer, liver cancer and colorectal cancer. MCP appears to bind to Gal-3 present on the surface of tumor cells and in the stromal tumor microenvironment, both solid and non-solid, which inhibits those tumors from developing or transforming, Azemar et al, *Oncology*, 1, 73-80 (2007).

Accordingly, those of skill in the art were aware of two well tolerated, non-toxic agents, honokiol and MCP, both substances commercially available in high levels of purity, that are effective as anti-cancer agents. They are administrable over a wide variety of protocols, including IM, IV and intraperitoneal administration, as well as subcutaneous administration and by adsorption through mucosal membranes, desirably through rectal and vaginal suppositories. Perhaps most importantly, they have been shown to be effective as orally administered, and may be taken daily, in one dose or in multiple doses per day, as part of a dietary regimen. They have been demonstrated to be safe and effective over a wide range of dosages, with honokiol being shown as effective over 5-500 mg/kg/day, and MCP at levels of 10-700 mg/kg/day (1-50 g/day), with an optimum level, for exhibiting effectiveness against cancer, at about 45-300 mg/kg/day (3-20 g/day.)

Importantly, in the '541 patent, the agents were shown to act synergistically in the control of cancer tumors and the inhibition of metastatic transformation of those cancers. Thus, the subject matter of the invention targeted in that case was the administration of synergistic amounts of honokiol and MCP to those in need of inhibition of tumor growth or metastatic transformation of those tumors, as well as that synergistic combination.

Honokiol down regulates the DNA expression of a complex array of signaling molecules and pathways, including numerous pro-inflammatory, proangiogenic cytokines and growth factors. For example, honokiol inhibits NFχB which has downstream effects on the cytokines TNF-α, IL-1β, IL-6, IL-12, IL-17, IL-18, Th-1, Th-17, PGE-2, IL-8 and others. Honokiol influences STAT3 with downstream effects on iNOS, COX-2, MMP-3, MMP-9 and MMP-13. Honokiol inhibits EGFR which then reduces activity of adhesion molecules ICAM-1 and VCAM-1. Honokiol also influences cell cycle regulatory molecules via its influence on the mTOR pathway, including downstream effects on Cyclins (D1, D2 and E), CDK's (2,4,6), p21, p27 and others. Honokiol influences MAPK with effects on downstream pathway molecules including BAX, BAD, Bcl-XL, Caspases (3,8,9) 15-LOX-1, PARP, p53, PPAR-γ and others, Arora et al. *Curr Mol Med*. December; 12(10):1244-52 (2012). Honokiol, influences energy metabolism, cell cycle regulation, anti-oxidation, etc. to promote normal intracellular functions. Honokiol promotes normal mitochondrial function by influencing mTOR, AKT, AMPK pathways that control energy pyruvate delivery to the mitochondria. The intracellular signaling pathways influenced by honokiol translate to the cell membrane communication system where they interact with proteins on both sides of the membrane.

As noted, MCP has been shown to bind to, and can be used to reduce the level of, Gal-3 in humans. This is discussed in detail in U.S. Pat. No. 8,764,675 which is directed to the apheresis of Gal-3, the disclosure of which is incorporated herein-by-reference. The variety of pathways mediated, to some degree, by Gal-3 are discussed there, as well as in U.S. patent application Ser. No. 13/153,648, currently pending, the entirety of which is incorporated herein-by-reference. Of particular note is the demonstrated ability of MCP to inhibit or reduce inflammation by binding to Gal-3.

Extracellular Gal-3 is relevant here via binding to the cell membrane glycoproteins and glycolipids receptors where it takes over control of communication, signaling back and forth across the cell membrane blocking cell surface receptors, hijacking normal signaling pathways. Gal-3 disrupts normal communication and has the properties of forming pentamers via its N-terminal domain leaving the carbohydrate recognition domains (CRD) on each molecule free to bind to numerous cytokines, growth factors etc. in the extracellular matrix milieu, active in the tumor microenvironment promoting cell-cell adhesion, inflammation, angiogenesis, etc. Gal-3 is also secreted by stromal cells and macrophages in the tumor microenvironment.

Gal-3 plays a central role in chronic inflammation and progression of inflammation to fibrosis; activates fibroblasts, the cells responsible for fibrogenesis/fibrosis, deFilippi et al. *E Cardiol Rev.* 6:33-36 (2010). At elevated levels in the circulation, Gal-3 is involved in myofibroblast proliferation, inflammation and fibrogenesis, tissue repair, and ventricular and tissue remodeling. Elevated blood levels are associated with higher risk of death in acute decompensated heart failure and chronic heart failure patients, de Boer et al. *Eur J Heart Fail.* 11:811-7 (2009). Gal-3 has been shown to be associated with inflammation and contributes to the progression of autoimmune disease in studies of rheumatoid arthritis, Ohshima et al. *Arthritis Rheum.* 48(10):2788-95 (2003).

MCP blocks Gal-3 activity that drives fibrosis by reducing macrophage activity, pro-inflammatory cytokine expression, and apoptosis, as well as lowering inflammatory markers thereby reducing tissue fibrosis. MCP reduces Gal-3 expression and disease severity in experimental acute kidney injury, Kolatsi-Joannou et al. *PLoS One.* April 8; 6(4): e18683 (2011). Gal-3 overexpression was required for inflammatory and fibrotic responses induced by aldosterone, causing arterial stiffness, hypertrophy, and fibrosis, thereby increasing the risk of heart failure. These changes were reversed with the use of oral MCP via a reduction in Gal-3 expression, Calvier et al. *Arterioscler Thromb Vasc Biol.* January; 33(1):67-75 (2013). Mice deficient in Gal-3 eating a high cholesterol diet showed over 50% reduction in aortic plaque formation. Administration of MCP during the latter stage of atherosclerosis reduced plaque volume, MacKinnon et al. *Glycobiology.* June; 23(6):654-63 (2013).

In experimental hyperaldosteronism, the increase in Gal-3 expression was associated with cardiac and renal fibrosis and dysfunction but was prevented by MCP or genetic disruption of Gal-3. MCP treatment reversed all of these effects of cardiac and renal hypertrophy (at morphometric, cellular, and molecular levels) and dysfunction in hypertensive aldosterone-salt-treated animals, 21. Calvier et al. *JACC Heart Fail.* January; 3(1):59-67 (2015). Aldosterone-salt-treated animals presented hypertension, cardiac inflammation, and fibrosis that were prevented by the inhibition of Gal-3 with MCP, Martinez-Martinez et al. *Hypertension.* October; 66(4):767-75 (2015). Gal-3 inhibition with MCP reduced cardiovascular levels of Gal-3, total collagen, collagen I, transforming and connective growth factors, osteopontin, and monocyte chemoattractant protein-1 in the heart and aorta of obese animals, Martinez-Martinez et al. *Hypertension.* November; 66(5):961-9 (2015).

Extracellular matrix (ECM) remodeling of the adipose tissue plays a pivotal role in the pathophysiology of obesity. In adipose tissue, obese animals presented an increase in Gal-3 levels that were accompanied by an increase in pericellular collagen. Obese animals exhibited higher adipose tissue inflammation as well as enhanced differentiation degree of the adipocytes. Treatment with MCP prevented all these effects.24 Inhibition of Gal-3 and aldosterone can reverse isoproterenol-induced left ventricular dysfunction, by reducing myocardial inflammation and fibrogenesis.

MCP can attenuate liver fibrosis through an antioxidant effect, inhibition of Gal-3 mediated hepatic stellate cells activation and induction of apoptosis. A study aimed at testing MCP's effect on liver fibrosis progression in a carbon tetrachloride (CCl4) injury model using separate groups. Animals were intraperitoneally injected, twice a week for 8 weeks with CCl4. Concurrently, MCP was administered daily in drinking water from the first week in a prophylactic model and in the beginning of week 5 in a therapeutic model. Interestingly, the therapeutic MCP late administration significantly decreased malondialdehyde (MDA), TIMP-1, Col1A1, α-SMA, and Gal-3 levels and increased levels of FAS, Cas-3, GSH, and SOD. It also decreased the percentage of fibrosis and necroinflammation significantly, Abu-Elsaad et al. *Can J Physiol Pharmacol.* May; 94(5):554-62 (2016).

Gal-3 has been shown to aggravate joint inflammation and destruction in experimental arthritis. Gal-3 expression in human synovial fibroblasts obtained from rheumatoid arthritis and osteoarthritis patients was inhibited with MCP. MCP reduced IL-6 levels in a dose-dependent manner, Arad et al. *Cytokine*. May; 73(1):30-5 (2015).

Thus, the level of skill in the art recognizes the existence of two unrelated anti-inflammatory compounds—honokiol and MCP. The two compounds appear to inhibit or reduce inflammation through different pathways, and by interaction with different biological agents. This offers the possible opportunity to co-administer the two compounds without inhibiting the effectiveness of either.

SUMMARY OF THE INVENTION

This invention addresses methods of inhibiting or reducing excessive inflammation in a mammal—inflammation that may either be hazardous to health, or result in discomfort or disfigurement of a mammalian patient without a corresponding benefit. Thus, the first aspect of the invention is the selection of an appropriate patient, be it a human, primate, commercial or companion mammal, that is in need of inhibition of, or reduction of, excess inflammation. It should be noted that identification of a suitable mammalian patient is distinguished from diagnosis of a mammal as suffering from inflammation. The level of diagnostic skill in the art of inflammation is high—it is often difficult to identify and distinguish a patient in need of inhibition or reduction of inflammation from one experiencing inflammation but possibly benefiting from it, or at least not requiring inhibition or reduction of the inflammation. Where this application speaks to "identifying" a mammalian target as in need of inhibition or reduction of inflammation, it refers to simply selecting or noting that a is intended to indicate that a patient diagnosed or characterized as suffering from excess inflammation may be treated by this invention. The step of identification is generally simply a comment, statement or representation that a person with inflammation may benefit from the treatment described.

In general, diagnosis of a mammal in need of inhibition or reduction of inflammation is made by a physician or veterinarian. Identifying a patient for treatment through this invention is a more straightforward task of noting that a patient previously diagnosed with inflammation may be selected for treatment in the method claimed herein. This does not require a medical doctor's skill—a patient, previously diagnosed as in need of treatment for inflammation—is selected—by that patient, or by literature or another individual, as suitable for treatment in this manner. Oftentimes a company will provide literature that suggests patients diagnosed with or characterized by inflammation can be advantageously treated using a specific course or agent. That is the sense in which identify is used in this application.

In some cases, inflammation may be life threatening and acute—cardiac tissue inflammation and nerve tissue inflammation often present challenges of this type. Often inflammation is chronic and not acute, but persistent, painful and inhibiting—a good example is arthritis. A large number of diseases are associated with, or characterized by, inflammation. Examples include Crohn's disease, asthma and a wide variety of diseases. Thus, while virtually all diseases mediated by foreign invaders, typically a virus, bacterium, parasite, or helminth, and many diseases mediated by the body's own systems—autoimmune diseases, many cancers—are associated with some degree of inflammation, in some situations the inflammation may be innocent or beneficial. Where inflammation tends to be run away, interferes with the body's ability to address the trauma, injury or disease, or interferes with medication intended to remedy or cure the situation, that individual may be in need of inhibition or reduction of inflammation.

Another condition characterized by excessive inflammation is gingivitis. This disease of the gums is initially triggered by the formation of plaque on the teeth and gums which generates toxins. These toxins irritate the flesh of the gums, causing them to bleed in response to slight pressure, such as tooth brushing. People who smoke or chew tobacco are more likely to have periodontal disease. Other risk factors include certain medications such steroids, anti-seizure drugs, cancer therapy drugs, blood pressure pills and birth control pills that affect the gums and people with systemic diseases such as diabetes, blood disorders, HIV and AIDS, that can lower the body's resistance to infection. Teens, pregnant women and those taking birth control pills face changes in the body's hormone levels, which can cause gum tissue to become more sensitive to the toxins produced by bacteria. If left untreated, gingivitis may lead to more serious, destructive forms of periodontal disease. It is estimated that more than 50% of the adult U.S. population exhibits gingivitis at any given time.

The inventor has demonstrated that in individuals in need of inhibition or reduction of inflammation, the co-administration of honokiol and MCP may be synergistic in their reduction of inflammation experienced. In other words, administering a given weight of honokiol and a given weight of MCP to a patient in need of the reduction or inhibition of inflammation results in a degree of reduction or inhibition of inflammation in that individual greater than would be expected by adding the anticipated reduction of inflammation due to the administration of honokiol and the anticipated reduction of inflammation due to the administration of MCP. This development is not predicted by, or suggested by, the action of either agent, alone. Administration is used in this application in its plain and ordinary sense, to mean given or provided, in the sense of a medical therapy. These formulations are not subject to extensive regulation, and so administration may comprise no more than selling or providing the composition comprising honokiol and MCP in amounts that synergistically coact to reduce or inhibit inflammation.

While the inventor does not wish to be bound by this theory, the explanation of the synergistic impact of the co-administration of these two agents may be due to the multiple pathways mediated by Gal-3. Thus, binding Gal-3 may be responsible not only for reducing the direct action of certain inflammatory agents, but it may open the pathway for action by other agents. In this fashion, binding of Gal-3 by MCP or other Gal-3 blockers, may in fact make it possible for honokiol to be active in venues and modes that are otherwise simply not available to other actions mediated by Gal-3. This has been seen in other situations involving other agents, such as tumor microenvironments, where Gal-3 may act not only as an external factor in terms of cell communication but in the suppression of agents such as TNF. Ruvolo et al. *Biochimica et Biophysica Acta*. March; 1863 (3):427-37 (2016) and in cardiac remodeling, where Gal-3 blockade may have wide ranging impacts not only inflammation but on fibrosis development, Martinez-Martinez et al. *Hypertension* October; 66(4):767-75. (2015). The unique combination of honokiol and MCP/Gal-3 blockers is that the anti-inflammatory properties of MCP/Gal-3 blockers encompasses extracellular actions and can effect both an individual cell as well as the intercellular space and matrix, the circulation, and the interactions between cells and between cells and the immune system. It can also mediate multiple inflammatory modifiers and enhancers such as TGF-β, TNF-α, NFκB, Fibronectin, Integrins, VEGF, and others. This can enhance the anti-inflammatory properties of honokiol that exerts multiple effects through intracellular pathway modifications as outlined in this application. As honokiol has unique and selective anti-inflammatory and antioxidant properties in the normal cell, while being a proxidant in the P-53 mutated cancer cell, Gal-3 blockage can enhance both the anti-inflammatory and antioxidant benefits of honokiol on multiple tissues, and its anticancer effects in multiple cancer tissues, especially those cancers that are inflammatory in nature. These unique synergistic benefits can be applied to multiple conditions that include cancer, and particularly inflammatory or inflammation enhanced cancers, degenerative diseases that involve inflammation or/and inflammation and fibrosis, autoimmune diseases, circulatory and cardiovascular diseases, neurological diseases (such as Parkinson's, multiple sclerosis, amyotrophic lateral sclerosis (ALS), Alzheimer, dementia, stroke) and others. As such it can help be used in the treatment of chronic kidney disease, pulmonary hypertension and fibrosis, cardiomyopathy, coronary artery disease, peripheral artery disease, hepatitis, inflammatory bowel disease, gastritis, among others. It can be of benefit in multiple infectious diseases, as Gal-3 blockers/MCP can help expose the infectious agent while Honokiol can exert direct anti-inflammatory and antimicrobial benefits. Gal-3 creates a lattice that helps the microbial agent shield itself from the immune system. This can be broken by MCP/Gal-3 blockers. As such it can be used for periodontitis, chronic infections of multiple origins (bacteria, fungal, helmenthic, parasitic, spirochetes, Lyme, *Babesia, Bartonella*, Lyme co-infections), gingivitis and others. It can also be used for ophthalmic diseases such as macular degeneration, cataracts, retinal diseases.

In a fashion still under investigation, the binding of Gal-3 by MCP may not only reduce the inflammation directly mediated by Gal-3, it may make it possible for honokiol to act in a pathway, or on the cells and organelles normally blocked by Gal-3 and the myriad pathways and interactions it mediates in the body. Those of skill in the art will recognize that the presence of Gal-3 is essential for mammalian life to some degree, and that those actually in need of the inhibition or reduction of inflammation will receive the combined administration of honokiol and MCP under a skilled artisan's care, so as to achieve reduced levels of inflammation without further injury or insult.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention. Where the Figures reflect the combined administration of MCP and honokiol (H), they are co-administered in a 9:1 ratio (by weight). Because patient perceptions vary broadly, the study addressed herein focuses on inflammation indices and indicators, rather than gross inflammation.

FIG. 1 reflects the effectiveness of tested agents inhibiting TNF-α synthesis. TNF-α (pg/ml) is induced profusely by LPS treatment of monocytes and the inhibitory effect of products on the TNF-α. MCP:H (9:1) combination showed noticeable inhibition whereas MCP alone does not possess any inhibitory effect on TNF-α synthesis.

DETAILED DESCRIPTION OF THE INVENTION

In the inflammatory cascade, the role of TNF-α and NFκB activity is well documented, Lawrence. *Cold Spring Harb Perspect Biol*. December; 1(6):a001651 (2009); Baeck and Tacke. *EXCLI Journal February* 7; 13:67-81 (2014). TNF-α has been identified as a major mediator of inflammatory processes, one of the most dramatic being gram-negative endotoxic shock, Paul et al. *Drug Discov Today* August; 11(15-16):725-32 (2006). This cytokine mediates early-stage responses of inflammation by regulating the production of other cytokines, including interleukin-1 (IL-1) and IL-6. Because TNF-α is the main mediator for a number of inflammatory toxic responses to chemicals, it represents a promising target for the prevention of inflammatory toxicity. TNF-α has also been reported to induce NFκB production and this protein is inhibited by the presence of antioxidants, Osborn et al. *Proc Natl Acad Sci USA*. April; 86(7):2336-40 (1989); Beg et al. *Mol Cell Biol*. June; 13(6):3301-10 (1993). NFκB is present in the cytoplasm as an inactivated dimer (I-kB) composed of p65 and p50 subunits. In response to inflammatory stimuli, I-kB is phosphorylated and degraded, and NFκB is released and translocated into the nucleus, Schottelius A J and Baldwin A S (Jr). *Int J Colorectal Dis*. February; 14(1):18-28 (1999). Because the expression of many inflammatory genes, including TNF-α, are known to be modulated by the binding of NFκB to its specific promoter regions, it represents a good target for suppressing NFκB activity for the regulation of lipopolysaaccharide (LPS)-induced inflammation, Baima et al. *J Biol Chem*. April 30; 285(18):13498-506 (2010).

Inhibition of LPS-Induced TNF-α Production by Honokiol (H), Modified Citrus Pectin (MCP) and MCP:H (9:1)

Pro-inflammatory cytokines are involved in the pathogenesis of a large number of disease processes. Interleukin 6 (IL-6) and tumor necrosis factor-α (TNF-α) are two multifunctional pro-inflammatory cytokines that are involved in the pathogenesis of inflammation, cardiovascular diseases, cancer and neurodegenerative disease through a series of cytokine signaling pathways. Hence, inhibition of such cytokines has currently become a major target of drug development. It is, however, important that such potential therapeutic agents demonstrate inhibitory bioactivity with respect to these cytokines.

Procedure:

Mouse monocyte cell line ($0.5 \times 10^6$/ml) was starved overnight by growing in MEM containing 0.5% medium and antibiotics. On the following day, the plates were replaced with fresh starving medium and treated with increasing concentrations of H, MCP and MCP:H (0-5000 µg/ml) in the presence and absence of lipopolysaccharide (LPS, 20 ng/ml). The compounds tested H, MCP and MCP:H were added initially and after incubation for 2 h at 37° C., LPS was added to induce inflammation. The plates were incubated for an additional 4 h and culture medium was collected, centrifuged and stored at −80° C. TNF-α produced and secreted into the medium by the cells was analyzed by ELISA procedure using the Quantakine kit from R&D systems, MN. Manufacturer's protocol was used for the analysis.

Figure 1:
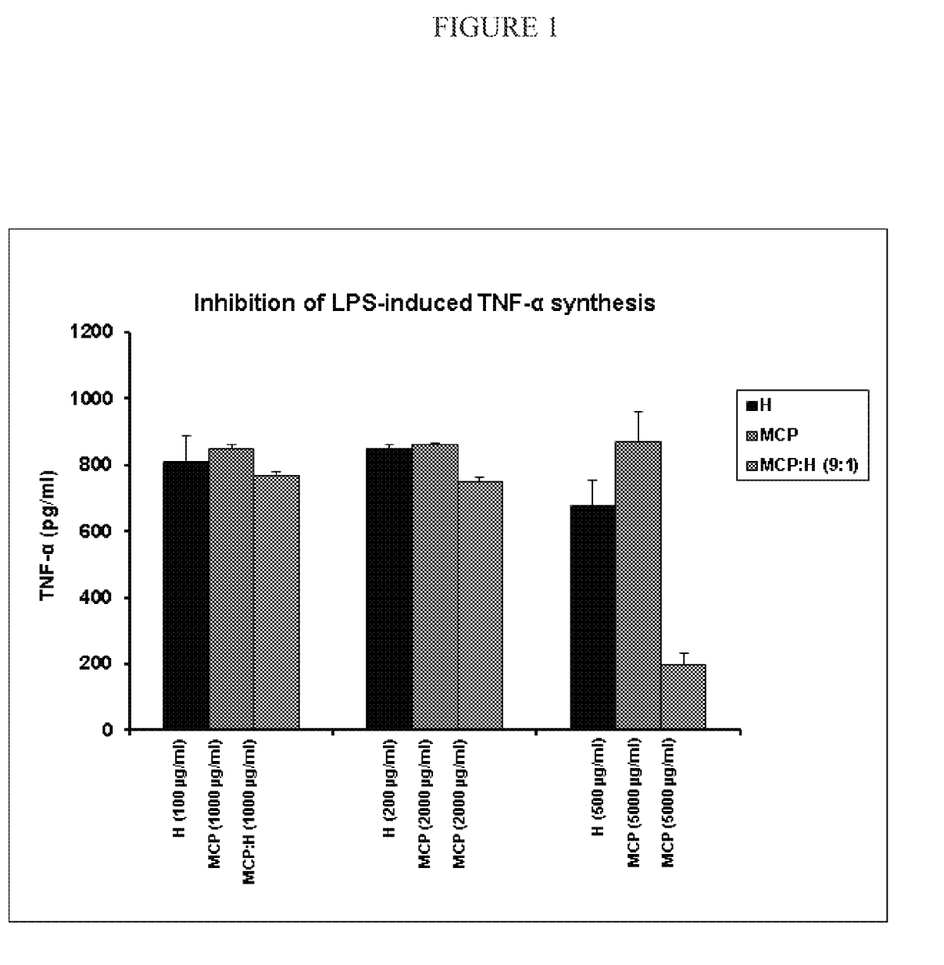
Figure 2:
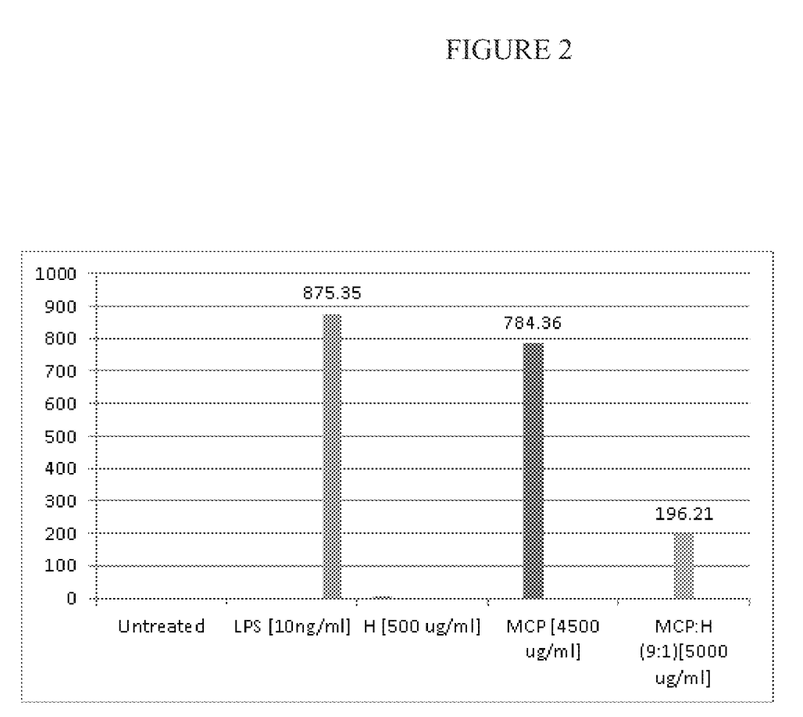
FIG. 2 is a chart reflecting TNF-α synthesis inhibition on an agent-by-agent basis.
Figure 4:
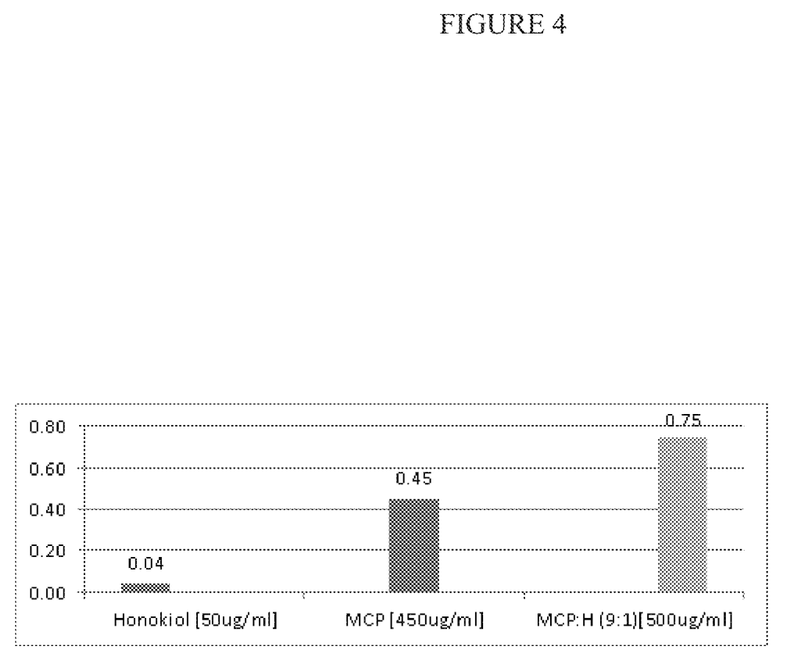
FIG. 4 is a chart that reflects the synergistic effect of honokiol and MCP on inhibition of TNF-α production

Results:

TNF-α (pg/ml) is induced profusely by LPS treatment of monocytes and the inhibitory effect of products on the TNF-α is shown in FIG. 1. The MCP:H (9:1) combination showed noticeable inhibition whereas MCP alone does not possess any inhibitory effect on TNF-α synthesis. Inhibition of TNF-α synthesis is also shown in FIGS. 2 and 4.

Antioxidant Activity of H, MCP and MCP:H (9:1)

Free radicals or reactive oxygen species (ROS) are produced during biochemical redox reactions as part of normal physiological cell metabolism (protection from infectious organisms) and as a response to environmental factors. ROS attack cellular components causing damage to lipids, proteins, and DNA which can initiate numerous diseases, including cancer, atherosclerosis, rheumatoid arthritis, diabetes, liver damage, and CNS disorders.

Since antioxidants neutralize the ROS, antioxidant activity of the nutraceutical would be of importance for product development. The principle underlying the antioxidant assay is formation of a ferryl myoglobin radical from metmyoglobin and hydrogen peroxide, which oxidizes ABTS (2,2'-azino-bis(3-ethylbenzthiazoline-6-sulfonic acid) to produce radical cation, ABTS+, a soluble chromogen that is green in color and can be determined spectrophotometrically at 405 nm. Antioxidants suppress the production of the radical cation in a concentration dependent manner and the color intensity decreases proportionally. Trolox, a water soluble vitamin E analog, is used as a control antioxidant for analyzing the antioxidant activity of other nutraceuticals/compounds.

Procedure:

Microplate assay was used for the analysis of antioxidant activity with different products according to the procedure described in the Antioxidant assay kit (Sigma-Aldrich, St. Louis, Mo.). The relative antioxidant concentration (mM equivalent of Trolox standard) was calculated from the absorbance readings.

Figure 3:
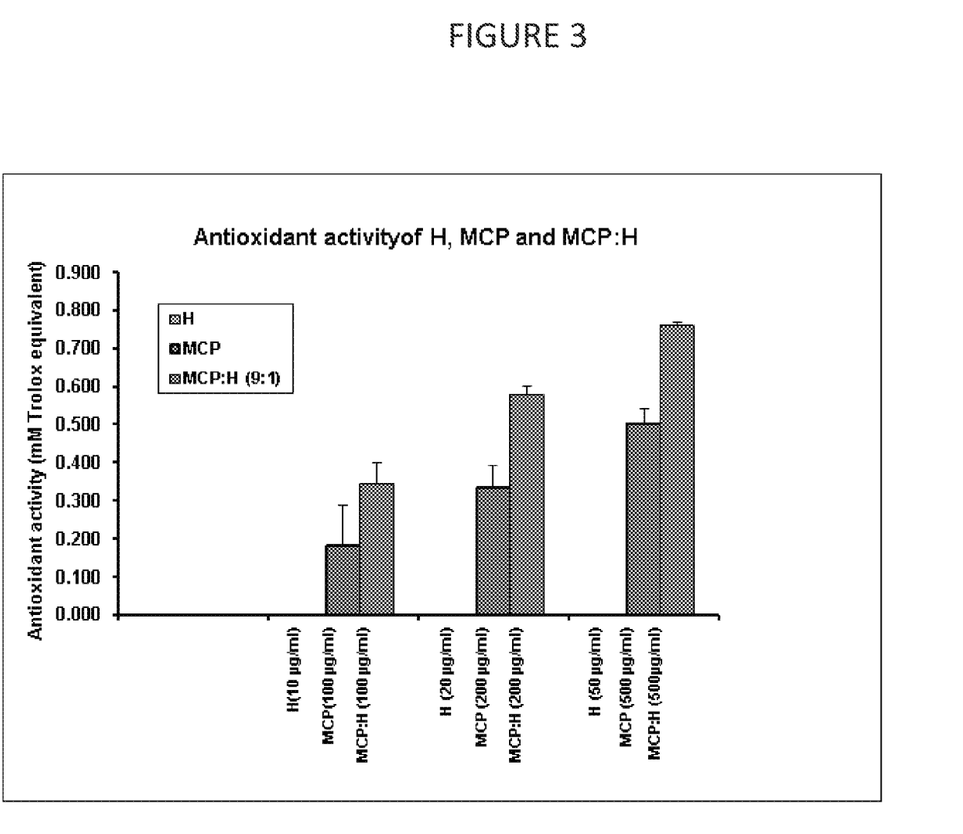
FIG. 3 is a chart of results reflecting the dose-dependent increase in the antioxidant activity seen using Trolox, a water-soluble vitamin E analog, as a control antioxidant for analyzing the antioxidant activity.

Results:

A dose-dependent increase in the antioxidant activity was noticed which was similar to the pattern shown by Trolox. The MCP:H combination had the highest activity, followed by MCP alone. Honokiol showed the least anti-oxidant activity among various products. See FIG. 3.

NFκB Activation Inhibition by H, MCP and MCP:H (9:1)

The transcription factor NFκB is a key component for the inducible expression of a wide variety of cellular and viral genes that code for mediation of the immune and inflammatory response. Therefore, accurate monitoring of NFκB activation is crucial for drug development and signal transduction pathway studies. Following treatment of the cells with each compound, I-κB phosphorylation occurs and NFκB disassociates from the NFκB/IκB complex in the cytoplasm leading to its translocation into the nucleus from cytoplasm. NFκB binds with DNA and activates the transcription of various genes. The importance of NFκB transcription factors in human inflammation and certain diseases makes them attractive targets for potential therapeutics which can either inhibit NFκB or selectively activate an array of ant-inflammatory cytokine genes thereby altering the ratio of pro-inflammatory to anti-inflammatory proteins.

Procedure:

RAW 264.7 mouse monocytes ($10 \times 10^6$) were treated with increasing concentrations of H, MCP and MCP:H (0-2000 μg/ml) for three days. Nuclear fraction was prepared from treated cells using hypotonic buffer and 10% Nonidet P-40 solution. Nuclear pellet was lysed in complete lysis buffer and nuclear protein prepared for activation studies. The protein concentration was determined by Bradford assay. Nuclear extract equivalent to 20 μg protein was analyzed for NFκB activity using TransAM p65 NFκB activity assay kit (Active Motif, CA). The ELISA plates were read at 450 nm with a reference wavelength of 655 nm in a microplate reader. The increase/decrease in absorbance was plotted against compound concentrations.

Figure 5:
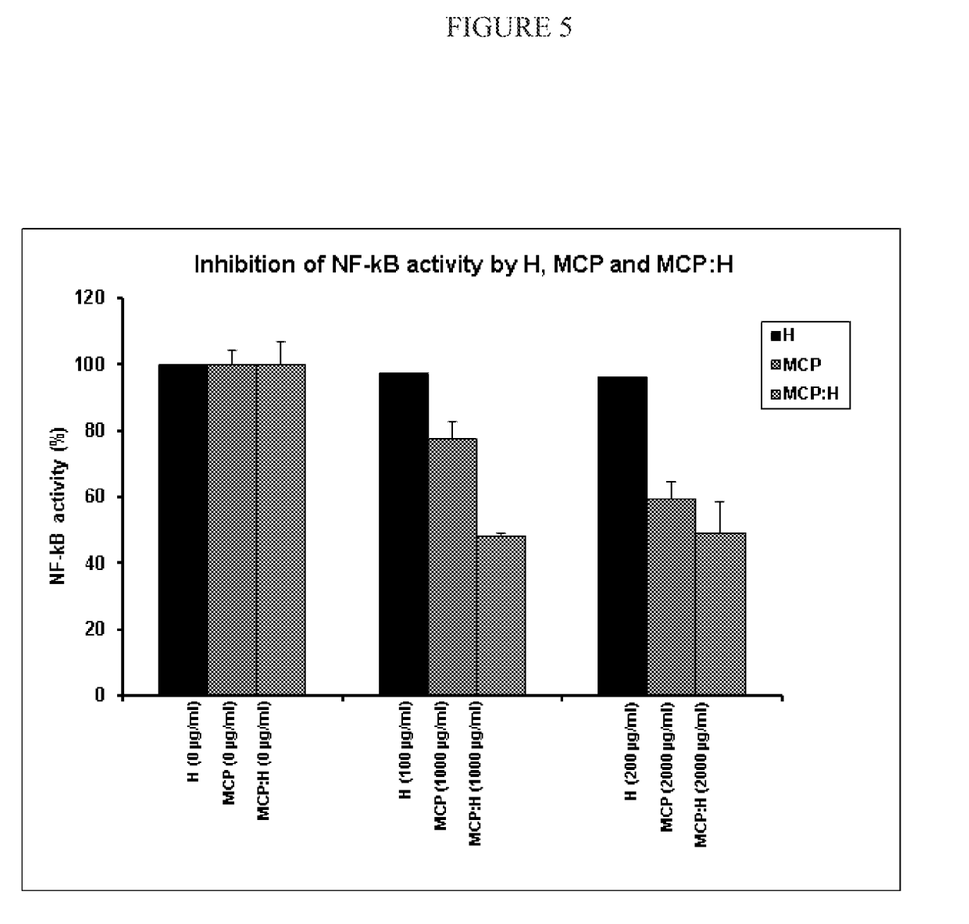
FIG. 5 is a chart that reflects the inhibition of NFκB activity for honokiol, MCP and their combination.
Figure 6:
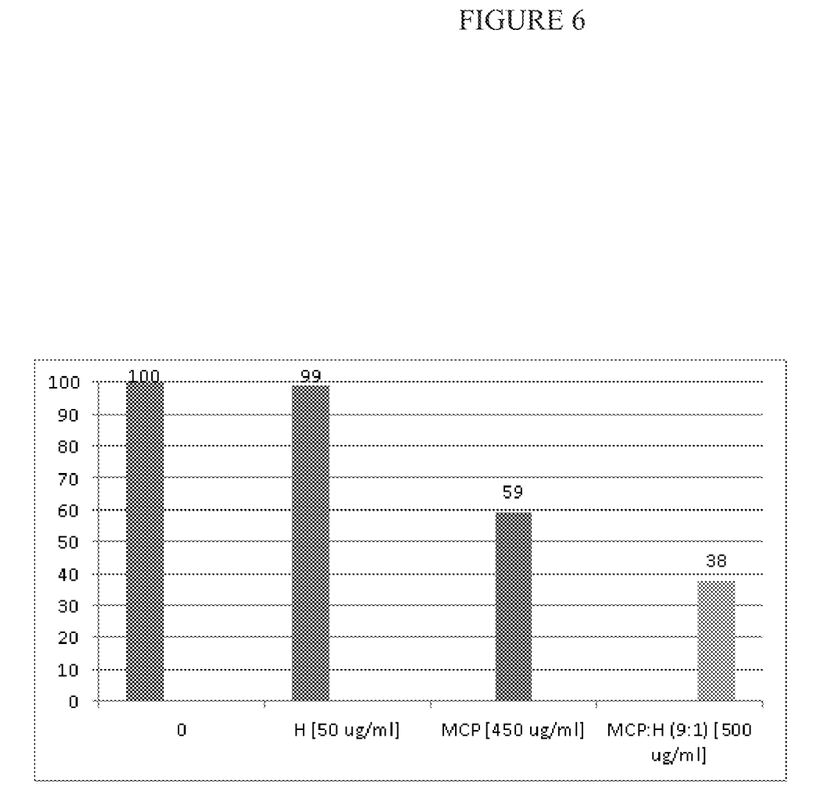
FIG. 6 reflects the % inhibition of NFκB (p65) activity on RAW264.7 mouse monocytes by the tested agents.

Results:

NFκB (p65) activity appeared to be inhibited by MCP:H (9:1) and MCP. Results reflecting the inhibition of NFκB are set forth in FIGS. 5 and 6.

Synergism/Additivity/Antagonism Between MCP and Honokiol

Data on TNF-α inhibition, antioxidant activity, effects on NFκB activity by MCP, H, and MCP:H (9:1) were analyzed using CompuSyn software in order to determine the synergism/additiveness/antagonism between MCP and H on these biochemical traits. The results are given in Table 1.

Results:

MCP and H have synergistic effect on inhibition of TNF-α production and antioxidant activity. MCP and H have very strong to strong synergistic effect on inhibition of NFκB activity with significant DRI values for both extracts. The drug reduction index shows the possible reduction in each of the extracts in a combination to achieve 50% effect (50% effective dose).

TABLE 1

Dose-effect relationship between Modified Citrus Pectin (MCP) and Honokiol (H)

| Biochemical traits | CI at $ED_{50}$ | CI at $ED_{75}$ | CI at $ED_{90}$ | DRI-MCP $ED_{50}$ | DRI-H $ED_{50}$ |
|---|---|---|---|---|---|
| Inhibition of LPS-induced TNF-α | 0.549 | 0.515 | 0.510 | 1.825 | 706.268 |
| Antioxidant activity | 0.670 | 0.546 | 0.446 | 33.682 | 1.562 |
| Inhibition of NFκB activity | 0.068 | 0.131 | 0.254 | 14.749 | 917.283 |

CI values by CompuSyn Analysis: <0.1=very strong synergism; 01-0.3=strong synergism; 0.3-0.7=synergism; 0.7-0.85=moderate synergism; 0.85-0.90=slight synergism; 0.90-1.10, nearly additive; 1.10-1.20=slight antagonism; 1.20-1.45=moderate antagonism; 1.45-3.3=antagonism; 3.3-10=strong antagonism; >10 very strong These studies continue to support the indication that, within the ranges indicated, MCP and honokiol show a synergistic effect in the reduction/inhibition of inflammation. Both MCP and honokiol are well tolerated over abroad range, and neither is associated with specific side effects within the contemplated range of (1-5,000 kilograms or more per day—?MCP.) Synergism, in the reduction of or inhibition of inflammation is broadly observed over this range, when administered in a ratio of about 8 (MCP:H) to about 10. Methods of administration are well known. As both MCP and honokiol are effective and well tolerated when administered orally, oral administration is preferred, and dosage ranges are provided here in oral equivalents, for humans. Other methods of administration include intravenous and intramuscular injections and via vaginal and oral suppositories. It is possible to simultaneously administer the MCP/honokiol combination or each of them separately through two difference modes of administration, for example MCP orally and honokiol IV. Given the information provided herein, those of skill in this art will arrive at appropriate dosage protocols for other targets, and select various ranges depending on whether the administration is for the purpose of addressing chronic or acute inflammation.

MCP binds very specifically to Gal-3. Not every Gal-3 binding agent is likely to combine synergistically with honokiol in the inhibition or reduction of inflammation as MCP dopes. There is, however, a short list of "equivalents"—compounds that bind to Gal-3 with about the same strength and with very similar specificity—that is, they bind to Gal-3 at the same point in the molecule, and with the same strength, as MCP. This list includes glycoproteins, glycolipids, β-galactosides, N-acetyllactosamine, Polysaccharide-based multivalent inhibitors, galactomannan oligosaccharides, C2-modified talose, GCS-100 (from La Jolla Pharma), thio-digalactosides 3,3'-di-triazol, GR-MD-02, a complex (galactoarabino-rhamnogalacturonan) polysaccharide polymer, offered by Galectin Therapeutics. In general, these "MCP equivalents" bind along or within the Gal-3 carbohydrate recognition domain.

As noted above, the combined administration of honokiol and MCP or 'MCP equivalent' can be administered to address inflammation in a variety of situations. One condition that permits of ease of administration is gingivitis. Oral rinses, mouthwashes, lozenges and related forms as well as toothpastes and the like can be used to introduce the inflamed tissue of the gums directly to the combination of MCP and Honokiol. Representative oral rinses, with other active agents, include those set forth in U.S. Pat. No. 5,707,610, incorporated herein by reference for its disclosure of effective rinses. Lozenges and pills and the like are set forth in U.S. Patent Publication US 2007/07187, also incorporated herein by reference for its teaching of solid forms of effective oral medications. The rinse, if a liquid form is selected, may be effervescent or still.

In a preferred embodiment, a 100 ml aliquot of mouthwash or oral rinse will comprise 1,0000 mg of MCP or "MCP equivalent" and 125 mg of honokiol, dissolved in a suitable water-based carrier. A patient rinses her mouth with one teaspoon of this preparation twice daily, or more often at need, for a period of two-three minutes. Thereafter, the rinse is spit out. Surfactants, flavorants and other agents may be added to the oral rinse to improve tolerance and achieve secondary goals. Flavorings are disclosed in the art incorporated herein by reference, but preferably include menthol and/or spearmint as essential oils. Reduction in inflammation should be detected relatively rapidly, in three days or so following the beginning of treatment.

'MCP equivalents' are identified by the degree to which they bind to gal-3. Thus, a candidate agent selected from the class of compounds including glycoproteins, glycolipids, β-galactosides, N-acetyllactosamine, polysaccharide-based multivalent inhibitors, galactomannan oligosaccharides, C2-modified talose, GCS-100 (from La Jolla Pharma), thio-digalactosides 3,3'-di-triazol, and GR-MD-02, is selected, and combined with gal-3 under conditions mimicking those found in the mammalian patients body. The resulting bond and complex is compared to the bond formed by MCP and gal-3 using standard assays. Potential equivalents which demonstrate a bond similar to or exceeding that of MCP in terms of strength or persistence will be useful in the claimed invention.

While the present invention has been disclosed both generically, and with reference to specific alternatives, those alternatives are not intended to be limiting unless reflected in the claims set forth below. The invention is limited only by the provisions of the claims, and their equivalents, as would be recognized by one of skill in the art to which this application is directed.

What is claimed is:

1. A method of treating gingivitis in a mammalian patient, wherein said method comprises: identifying a mammalian patient that can benefit from a reduction or inhibition of gingivitis, administering to the oral cavity of said patient a combination of honokiol and MCP in amounts that synergistically reduce or inhibit inflammation in said oral cavity, wherein said combination of honokiol and MCP is in the form of an oral rinse, lozenge, tablet, sucking candy or toothpaste.

2. The method of claim 1, wherein said administration of honokiol and
    MCP to the oral cavity is effected at least twice daily to inhibit or reduce gingivitis.

3. The method of claim 1, wherein said combination of honokiol and MCP is in the form of an oral rinse.

4. The method of claim 3, wherein said oral rinse is effervescent.

5. The method of claim 1, wherein said honokiol is administered in an amount, as oral equivalents, of 2-500 mg/kg of body weight/day and said MCP is administered, in oral equivalents, of 10-700 mg/kg/day.

* * * * *